United States Patent [19]

Masuda

[11] Patent Number: 5,365,286
[45] Date of Patent: Nov. 15, 1994

[54] OPHTHALMIC MEASURING APPARATUS

[75] Inventor: Takashi Masuda, Yamato, Japan

[73] Assignee: Canon Kabushiki Kaisha, Tokyo, Japan

[21] Appl. No.: 829,276

[22] Filed: Feb. 3, 1992

[30] Foreign Application Priority Data

Feb. 5, 1991 [JP] Japan .................. 3-036797

[51] Int. Cl.⁵ .............................. A61B 3/10
[52] U.S. Cl. ................... 351/204; 351/200; 33/200; 356/127
[58] Field of Search ............ 351/204, 205, 200; 33/200; 356/124, 127

[56] References Cited

U.S. PATENT DOCUMENTS 4,098,002  7/1978  Campbell et al. .......... 33/200
4,571,842  2/1986  Ikezawa et al. ........... 33/200
5,152,067 10/1992  Kurachi et al. ........... 33/200

FOREIGN PATENT DOCUMENTS 0115723  8/1984  European Pat. Off. .
0363281  4/1990  European Pat. Off. .

Primary Examiner—William L. Sikes
Assistant Examiner—Hung Xuan Dang
Attorney, Agent, or Firm—Fitzpatrick, Cella, Harper & Scinto

[57] ABSTRACT

An ophthalmic measuring apparatus includes a device for measuring the distance from a certain point (such as the center of the other of right and left spectacle lenses or the bridge position of the lenses) to the center of the lenses on the basis of the amount of displacement of a spectacle lens contacting member, and a device for measuring the distance from a certain point (such as the center of the pupil of the other of right and left eyes to be examined or the nose position) to the center of the pupil on the basis of the amount of displacement of an observation system for observing the front eye parts of the eyes to be examined therethrough.

28 Claims, 5 Drawing Sheets

FIG. 8A

```
PUPIL DIST.  68 mm    ←— DISTANCE OF PUPILS (1)
LENS DIST.   63 mm    ←— DISTANCE OF LENSES (2)
   DELTA      5 mm    ←— (1)−(2)
     R        1.25△ ⎫
     L        1.25△ ⎭ ←— PRISM POWER

SPH        −5.00D ⎫
CYL         0.00D ⎬ ←— MEASURED LENS POWER
AX            180 ⎭
```

FIG. 8B

```
REF PD : 68
    SPH    −6.25 ⎫
    CYL     0.00 ⎬ MEASURED REFRACTION
    AX       180 ⎭
LENS PD : 63
    SPH    −3.75 ⎫
    CYL     0.00 ⎬ MEASURED LENS
    AX       180 ⎭
    △PD : 5
    △SPH   −2.50 ⎫
    △CYL    0.00 ⎬ DIFFERENCE
    △AX      180 ⎭
```

OPHTHALMIC MEASURING APPARATUS

BACKGROUND OF THE INVENTION

1. Field of the Invention

This invention relates to an ophthalmic measuring apparatus used, for example, in ophthalmic hospitals or the like and having the function of measuring the distance between pupils, the function of measuring the inter-lens distance of lenses to be examined, and further the function of measuring the refractive values of the lenses to be examined.

2. Related Background Art

When prescribing spectacle lenses for a patient, it is of course important to measure the eye refractive values of eyes to be examined by an autorefractometer, to measure the vertex refractive values of spectacle lenses and inspect the fit of the spectacle lenses, as well as to inspect whether the difference between the distance between the pupils of the eyes to be examined and the inter-lens distance of the spectacle lenses is within an allowable range. This is because when this difference is great, a light beam entering the eye to be examined is not transmitted through the center of the spectacle lens and therefore deviation of the image and distortion and astigmatism by a prism action occur, thus causing two images to be seen and causing a reduction in sight and distortion. Moreover, in the case of spectacle lenses which are great in refractive power, even a slight difference greatly affects the patient.

So, in the past, the measurement of the inter-lens distance has been effected by the use of a method of measuring the distance between pupils by an inter-pupil distance meter utilizing reflected light beams from corneas, or a scale incorporated in an auto refractometer, and on the other hand, by printing marks at the centers of spectacle lenses in conjunction with a point printing function incorporated in a lens meter, and measuring the distance between the marks with a scale.

However, in such a system, the measurement of the refractive values of the eyes, the measurement of the refractive values of the spectacle lenses, the measurement of the inter-pupil distance, and the measurement of the inter-lens distance are effected by discrete apparatuses, and this is not preferable from the viewpoints of measurement efficiency and apparatus installation space, and is also subject to the risk of making a mistake in combining the measurement data. Also, as previously described, the allowable range of the difference between the inter-pupil distance and the inter-lens distance differs, depending on the refractive power of spectacle lenses and therefore, an overall judgment of the measurement data becomes necessary. But such a prior-art system suffers from the problem that this overall judgment is difficult to perform.

SUMMARY OF THE INVENTION

It is an object of the present invention to solve the above-noted problems peculiar to the prior art and to provide an ophthalmic measuring apparatus having the function of measuring the distance between the pupils of eyes to be examined and the distance between spectacle lenses and capable of detecting the prism power of the spectacle lenses.

It is also an object of the present invention to provide an ophthalmic measuring apparatus capable of measuring the refractive values of lenses and the refractive value of eyes to be examined.

BRIEF DESCRIPTION OF THE DRAWINGS

FIGS. 8A and 8B show examples of data display.

DETAILED DESCRIPTION OF THE PREFERRED EMBODIMENTS

Figure 1:
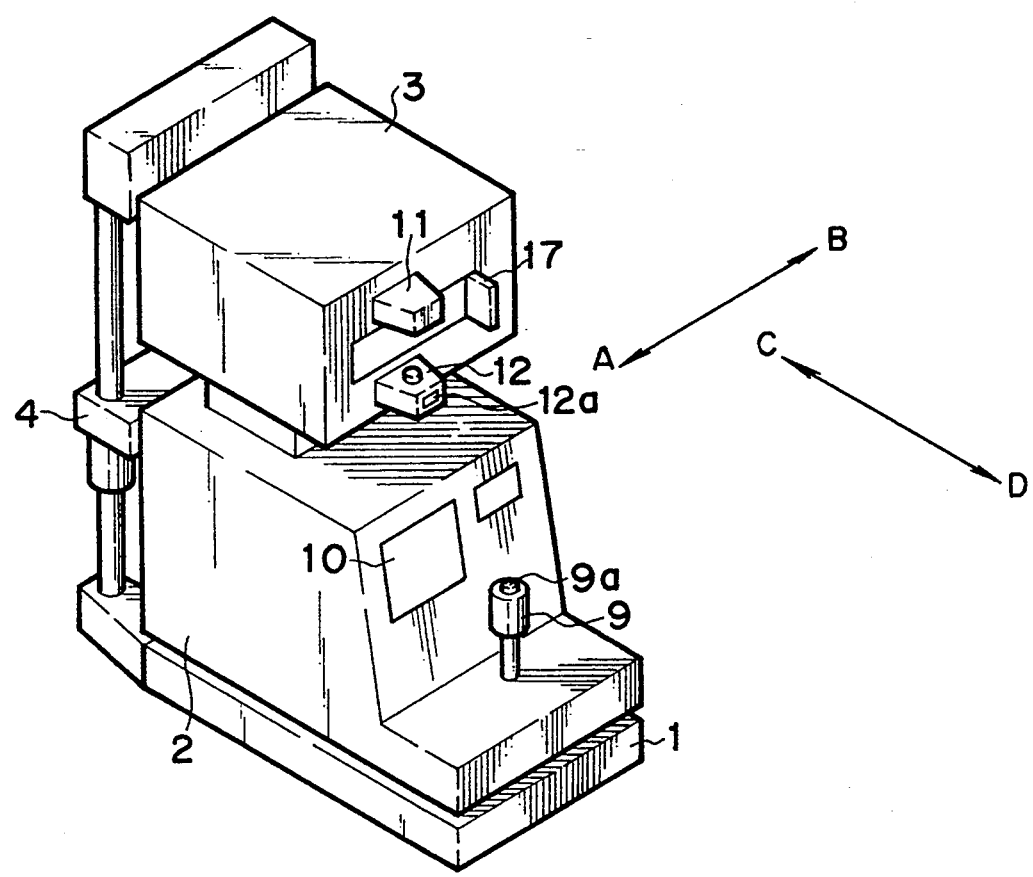
FIG. 1 is a pictorial view of an apparatus according to the present invention.
Figure 2:
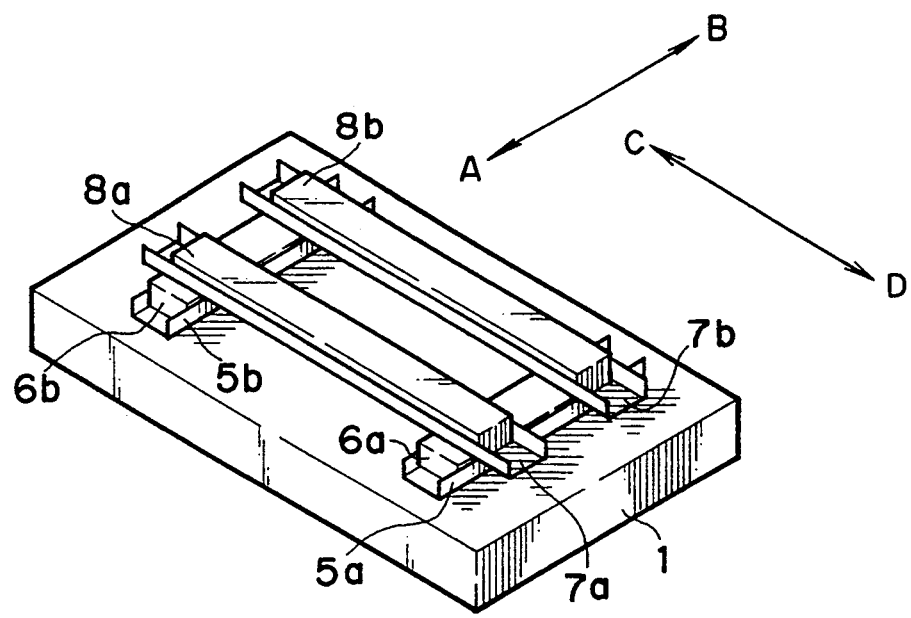
FIG. 2 shows the construction of a horizontal moving mechanism for a control unit of the present invention.

Referring to FIG. 1 which shows a pictorial view, a control unit 2 is provided on the examiner side of a fixed base 1 so as to be slidable in a horizontal plane, a measuring unit 3 is vertically movably placed on the control unit 2, and a face supporting bed 4 is fixed to the examinee side of the fixed base 1. As regards the connecting region between the fixed base 1 and the control unit 2, as shown in FIG. 2, a pair of right and left bearing members 5a and 5b are fixed to the upper surface of the fixed base 1 parallel to a direction A-B, i.e., the examinee's left to right direction, a pair of front and rear bearing members 7a and 7b are installed on right and left guide shafts 6a and 6b fitted to the right and left bearing members 5a and 5b, respectively, in parallelism to a direction C-D perpendicular to the direction A-B, and front and rear guide shafts 8a and 8b fitted to the front and rear bearing members 7a and 7b, respectively, are fixed to the lower surface of the control unit 2, with the result that the control unit 2 is horizontally movable on the fixed base 1 longitudinally and laterally.

Figure 3:
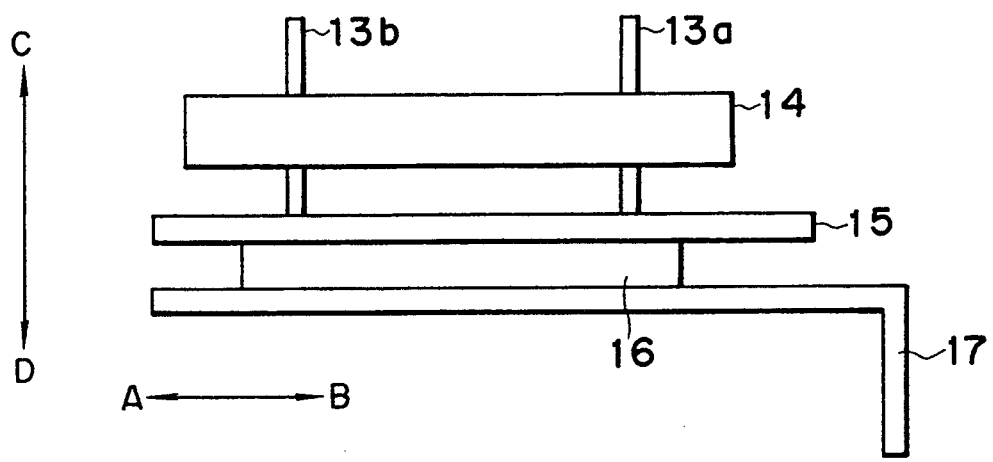
FIG. 3 shows the construction of a moving mechanism for a spectacle lens contacting member of the present invention.
Figure 4:
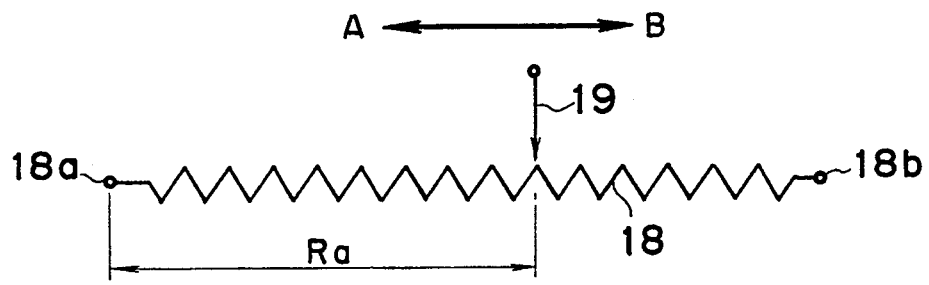
FIG. 4 illustrates a method of detecting the amount of movement of the spectacle lens contacting member of the present invention.

An operating rod 9 having a measuring switch 9a and a television monitor 10 are mounted on the examiner side of the control unit 2, and by the operation of the operating rod 9, the control unit 2 is slidable on the fixed base 1. Also, a light beam projecting portion 11 for the measurement of the refractive values of spectacle lenses and a light beam receiving portion 12 having a measuring button 12a are projectedly provided on the examiner side of the measuring unit 3, and a spectacle lens moving mechanism including a spectacle lens contacting member 17 as shown in FIG. 3 is provided between the light beam projecting portion 11 and the light beam receiving portion 12. That is, a guide shaft 14 having a set of parallel bearing members 13a and 13b movably inserted thereinto is fixed to the control unit 2, a base plate 15 is installed on the bearing members 13a and 13b, and the spectacle lens contacting member 17 bent at a right angle is mounted on the base plate 15 with a sliding member 16 interposed therebetween, the spectacle lens contacting member 17 being movable in the direction A-B and the direction C-D relative to the measuring unit 3. A brush 19 shown in FIG. 4 is fixed to the sliding member 16, and a linear potentiometer 18 having terminals 18a and 18b is fixed to the spectacle lens contacting member 17 so that when the spectacle lens contacting member 17 is moved in the direction A⇌B relative to the sliding member 16, the resistance value Ra between the terminal 18a and the brush 19 may vary and the amount of movement of the member 17 may be detected. A front eye part observation system containing a television camera in the measuring unit 3 for the measurement of the inter-pupil distance is provided on the measuring unit 3.

Figure 5:
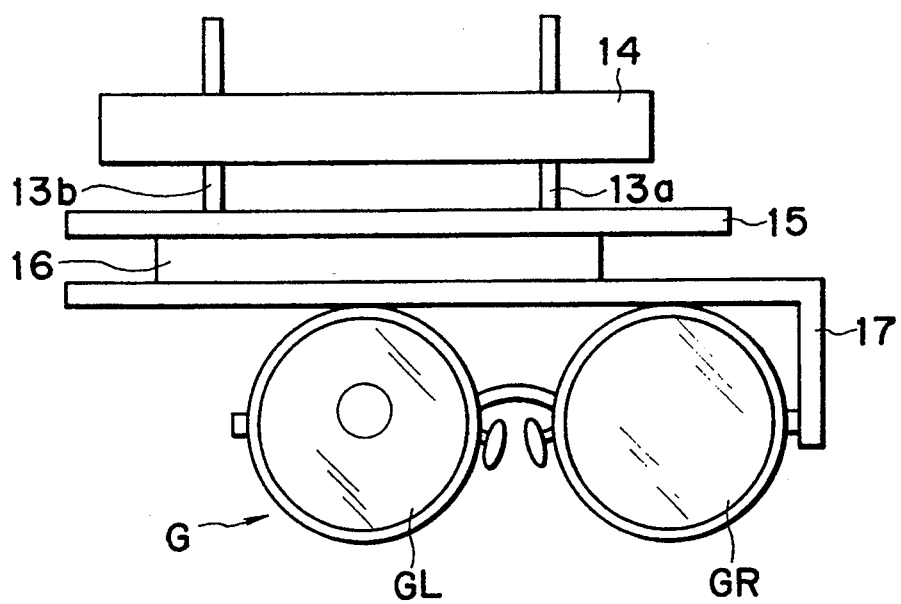
FIG. 5 illustrates a method of measuring the inter-lens distance according to the present invention.

During the measurement of the refractive values and inter-lens distance of a lens G to be examined, with the upper end portion and right end portion of the lens G to be examined brought into contact with the spectacle lens contacting portion 17 as shown in FIG. 5, the lens G to be examined is moved with the spectacle lens contacting member 17 and the center of the left lens GL is first brought into coincidence with the optical axis of a measuring optical system by a well-known method. The measuring button 12a is then depressed to thereby measure the refractive value of the left lens GL and simultaneously therewith, the resistance value Ra at that point in time is detected and stored. Subsequently, with the lens G to be examined held in contact with the spectacle lens contacting member 17, the positioning of the center of the right lens GR and the measurement of the refractive value of the right lens GR are likewise effected, and the resistance value Ra at that point in time is detected, and the inter-lens distance is measured from the amount of variation in the resistance value. The inter-lens distance of the individual right and left lenses (the distance from the center of the spectacles to the centers of the right and left lenses) is the distance between the two lenses multiplied by $\frac{1}{2}$.

During the measurement of the inter-pupil distance, the examinee's face portion is fixed on the face supporting bed 4 and the operating rod 9 is operated to move the control unit 2 on the fixed base 1 so that the center of the pupil of one of the eyes to be examined may come to a predetermined position in the optical system while the front eye part is displayed on the television monitor 10, and then the other eye to be examined is likewise positioned, whereby the inter-pupil distance is measured from the amount of left to right movement of the control unit 2. The distance between the individual right and left pupils (for example, the distance from the nose position to the centers of the right and left eyes to be examined) is the distance between the two pupils multiplied by $\frac{1}{2}$. Although the description of the method of detecting the amount of left to right movement is omitted herein, it may be accomplished by the utilization of a linear potentiometer as during the measurement of the inter-lens distance. That is, for example, the linear potentiometer 18 having the terminals 18a and 18b as shown in FIG. 4 is provided on the right guide shaft 6a of FIG. 2, and the brush 19 is provided on the right bearing member 5a side.

The prism power P of the spectacle lens is given by the following equation when the difference [mm] between the distance between the individual right and left lenses and the inter-pupil distance is Δd and the refractive power of the spectacle lens is D:

$P = \Delta d \cdot D / 10.$

If this prism power P is within an allowable range, the examiner judges that the spectacle lens is fit for the eye to be examined.

As previously described, the allowable amount of the difference between the inter-pupil distance and the inter-lens distance depends also on the refractive power of the spectacle lens and therefore, it is significant to measure these three by a single ophthalmic measuring apparatus and display them on the same television monitor 10. Where a well-known eye refractive power measuring system (a measuring system for projecting an index light beam onto the fundus of the eye to be examined and receiving the reflected light of the eye fundus by a light receiving system) is provided in the measuring unit 3, the measurement of the refractive value of the eye to be examined can also be effected at the same time and therefore, to greater convenience, the comparison between the refractive values of the eye to be examined and the spectacle lens can also be effected. It will be convenient if the measured values and the difference therebetween are displayed on the television monitor 10. If the examinee is made to wear a spectacle frame the center position of which is indicated in advance, the detection of the inter-pupil distance will become easy.

Figure 6:
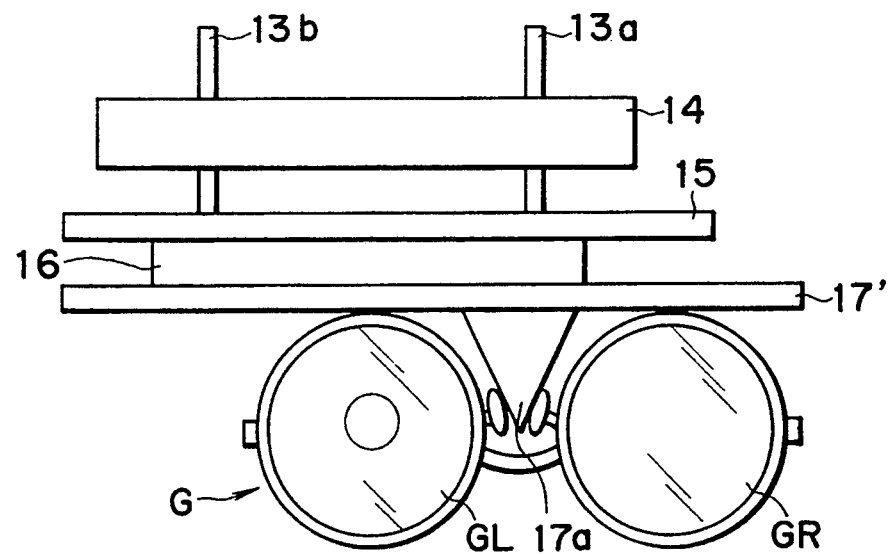
FIG. 6 illustrates a method of measuring the inter-lens distance in accordance with another embodiment.

Referring to FIG. 6 which shows a spectacle lens moving member according to another embodiment, a planar spectacle lens contacting member 17' is mounted in place of the spectacle lens contacting member 17, and a bridge supporting portion 17a is secured to the spectacle lens contacting member 17', and the examiner places and fixes the bridge of the lens G to be examined on the bridge supporting portion 17a. If the position in which the center position of the bridge supporting portion 17a coincides with the optical axis of the measuring optical system is stored as the reference position, the distance between the individual right and left lenses can be detected.

Referring to FIG. 6, which shows a spectacle lens signal processing circuit provided in the control unit 2 and the measuring unit 3, a data bus 20 provided for signal transmission has connected thereto an MPU 21 for effecting a calculation process, an ROM 22 for memorizing a control program, and an RAM 23 for temporarily memorizing measured values. The data bus 20 is connected to an inter-pupil distance measuring system through an inter-pupil distance measuring switch 24 and to an inter-lens distance measuring system through an inter-lens distance measuring switch 25, and the output of the inter-pupil distance measuring system is connected to the data bus 20 through an A/D coverter 26, and the output of the inter-lens distance measuring system is connected to the data bus 20 through an A/D converter 27. Further, a television camera 28 for photographing the front eye part of the eye to be examined is connected to the data bus 20 through a CRT controller 29, and the television camera 28 and the CRT controller 29 are connected to the television monitor 10.

When the inter-pupil distance measuring switch 24 is closed, the measurement of the inter-pupil distance is started and for example, the amount of variation in the potentiometer is input to the MPU 21 and the RAM 23 through the A/D converter 26, whereupon the inter-pupil distance is calculated. Likewise, when the inter-lens distance measuring switch 25 is closed, the measurement of the inter-lens distance is started, and the measured value is input through the A/D converter 27, whereupon the inter-lens distance is likewise calculated. The distance between the two measured values can also be calculated in the MPU 21, and those calculated values are combined with the image signal from the television camera 28 through the CRT controller 29 and the combined value is displayed on the television monitor 10. The two measured values together may be displayed on the television monitor 10 (see FIG. 8A). Also, the refractive values of the eye to be examined and the spectacle lens and the difference therebetween can be displayed on the television monitor 10 (see FIG. 8B).

As described above, the ophthalmic measuring apparatus according to the present invention has an inter-lens distance measuring function and the inter-pupil distance measuring function and therefore, has the effect that the measuring time is shortened and the judgment as to whether the spectacle lens is fit for the eye to be examined becomes easy by the comparison with the measured values.

What is claimed is:

1. An ophthalmic measuring apparatus comprising:
   a spectacles contacting member for contacting spectacles having a spectacle lens to be examined;
   optical characteristics measuring means for causing a light beam to enter the spectacle lens, and for effecting measurement of the optical characteristics of the spectacle lens;
   first distance measuring means for measuring the distance from a first position to the center of the spectacle lens on the basis of an amount of displacement of said spectacles contacting member; and
   second distance measuring means, providing with an observation system for observing the front eye part of an eye to be examined therethrough, for measuring the distance from a second position to the center of the pupil of the eye to be examined on the basis of the amount of displacement of said observation system.

2. An ophthalmic measuring apparatus according to claim 1, wherein said first position is the center position of the other of right and left spectacle lenses.

3. An ophthalmic measuring apparatus according to claim 1, wherein said first position is the bridge position.

4. An ophthalmic measuring apparatus according to claim 1, wherein said second position is the center position of the pupil of the other of right and left eyes to be examined.

5. An ophthalmic measuring apparatus according to claim 1, further comprising means for comparing the outputs of said first and second distance measuring means.

6. An ophthalmic measuring apparatus according to claim 5, further comprising means for displaying the output of said comparing means.

7. An ophthalmic measuring apparatus according to claim 1, further comprising means for displaying the outputs of said first and second distance measuring means.

8. An ophthalmic measuring apparatus according to claim 1, further comprising means for causing a light beam to enter the eye to be examined and for measuring the refractive value of the eye to be examined by the reflected light beam from the fundus of the eye to be examined.

9. An ophthalmic measuring apparatus according to claim 8, further comprising means for comparing said the measured refractive value of the spectacle lens and the refractive value of the eye to be examined with each other.

10. An optical measuring comprising:
    a spectacles contacting member for contacting spectacles to be examined;
    first distance measuring means for measuring the distance from a first position to the center of a spectacle lens of the spectacles to be examined on the basis of the amount of the displacement of said spectacles contacting member; and
    second distance measuring means, providing with an observation system for observing the front eye part of an eye to be examined therethrough, for measuring the distance from a second position to the center of the pupil of the eye to be examined on the basis of the amount of displacement of said observation system.

11. An ophthalmic measuring apparatus according to claim 10, wherein said first position is the center position of the other of right and left spectacle lenses.

12. An ophthalmic measuring apparatus according to claim 10, wherein said first position is a bridge position.

13. An ophthalmic measuring apparatus according to claim 10, wherein said second position is the center position of the pupil of the other of right and left eyes to be examined.

14. An ophthalmic measuring apparatus according to claim 10, further comprising means for comparing the outputs of said first and second distance measuring means.

15. An ophthalmic measuring apparatus according to claim 14, further comprising means for displaying the output of said comparing means.

16. An ophthalmic measuring apparatus according to claim 10, further comprising means for displaying the outputs of said first and second distance measuring means.

17. An ophthalmic measuring apparatus comprising:
    a spectacles contacting member for contacting spectacles to be examined;
    first distance measuring means for measuring the distance from a first position to the center of a first spectacle lens of the spectacles to be examined having first and second spectacle lenses on the basis of the amount of displacement of said spectacles contacting member;
    second distance measuring means for measuring the distance from a second position to the center of the pupil of a first eye of a patient to be examined; and
    means for comparing the distances measured by said first and second distance measuring means.

18. An apparatus according to claim 17, wherein said first distance measuring means measures the distance from a center of the second spectacle lens, as said first position, to the center of the first spectacle lens.

19. An apparatus according to claim 17, said second distance measuring means measures the distance from the center of the pupil of a second eye of the patient, as said second position, to the center of the pupil of the first eye to be examined.

20. An ophthalmic measuring apparatus comprising:
    a spectacles contacting member for contacting spectacles to be examined;
    distance measuring means for measuring the distance from a first position to the center of a first spectacle lens of the spectacles to be examined having first and second spectacle lenses on the basis of the amount of displacement of said spectacles contacting member;
    information providing means for providing information of the distance from a second position to the center of the pupil of a first eye of a patient to be examined; and means for comparing the distance from the second position to the center of the pupil with the distance measured by said distance measuring means.

21. An apparatus according to claim 20, said distance measuring means measures the distance from a center of the second spectacle lens, as said first position, to the center of the first spectacle lens.

22. An apparatus according to claim 21, said information providing means provides the information of the distance from a center of the pupil of a second eye of the patient, as said second position, to the center of the pupil of the first eye to be examined.

23. An ophthalmic measuring apparatus comprising:
first information providing means for providing information of the distance from a first position to the center of a first spectacle lens of spectacles having first and second spectacle lenses;
second information providing means for providing information of the distance from a second position to the center of the pupil of a first eye of a patient to be examined; and
display means for displaying the information provided by said first and second information providing means, said displaying means displaying the information so that an examiner can see the difference between the distance from the first position to the center of the first spectacle lens and the distance from the second position to the center of the pupil of the eye to be examined.

24. An apparatus according to claim 23, wherein said first information providing means provides information of the distance from a center of the second spectacle lens, as said first position, to the center of the first spectacle lens.

25. An apparatus according to claim 24, wherein second information providing means provides information of the distance from the center of the pupil of a second eye of the patient to be examined, as said second position, to the center of the pupil of the first eye to be examined.

26. An ophthalmic measuring apparatus comprising:
a spectacles contacting member for contacting spectacles to be examined;
first distance measuring means for measuring the distance from a first position to the center of a first spectacle lens of the spectacles to be examined having first and second spectacle lenses on the basis of the amount of displacement of said spectacles contacting member; and
second distance measuring means for measuring the distance from a second position to the center of the pupil of a first eye of an examinee.

27. An apparatus according to claim 26, wherein said first distance measuring means measures the distance from a center of the second spectacle lens, as said first position, to the center of the first spectacle lens.

28. An apparatus according to claim 26, said second distance measuring means measures the distance from the center of the pupil of a second eye of the examinee, as said second position, to the center of the pupil of the first eye to be examined.

* * * * *

UNITED STATES PATENT AND TRADEMARK OFFICE
CERTIFICATE OF CORRECTION

PATENT NO. : 5,365,286
DATED : November 15, 1994
INVENTOR(S) : Takashi Masuda

It is certified that error appears in the above-indentified patent and that said Letters Patent is hereby corrected as shown below:

COLUMN 2

Line 39, "in parallelism" should read --parallel--.

COLUMN 4

Figure 7:
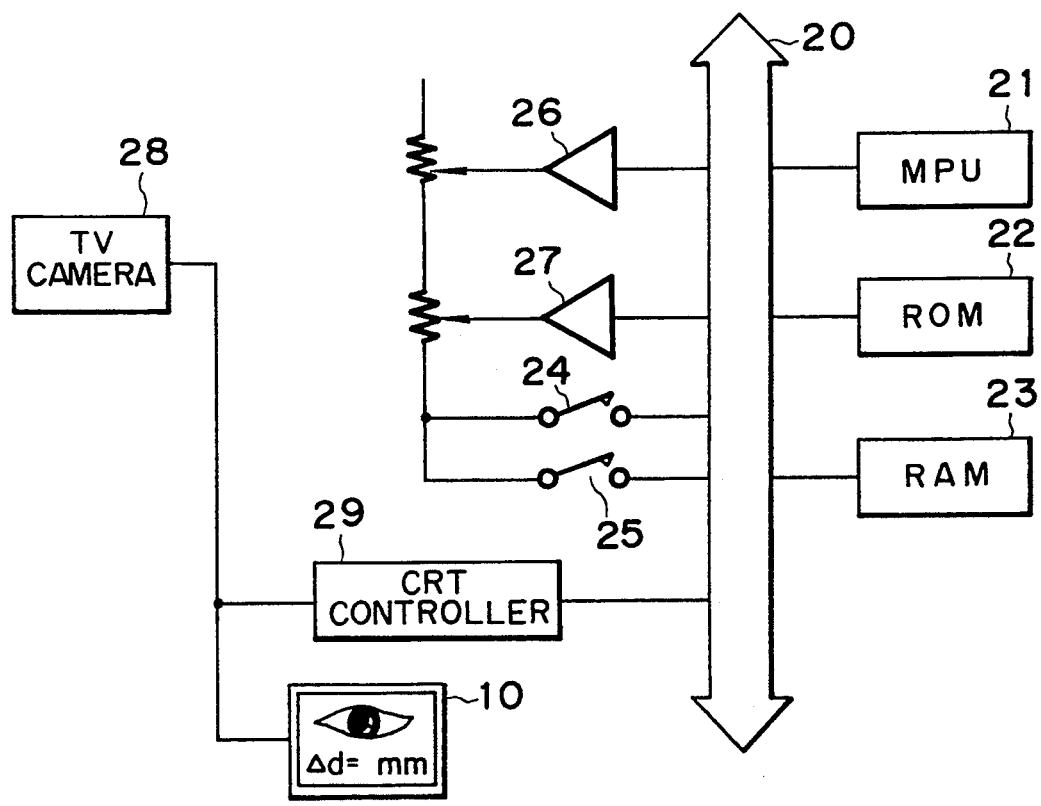
FIG. 7 shows the construction of a signal processing circuit of the present invention.

Line 22, "FIG. 6" should read --FIG. 6,--.
Line 35, delete in its entirely and substitute the following --Referring to FIG. 7 which diagrammatically shows a--.

COLUMN 5

Line 9,  "the" should read --an--
Line 62, "said" should be deleted.
Line 66, "measuring" should read --measuring apparatus--.

UNITED STATES PATENT AND TRADEMARK OFFICE
CERTIFICATE OF CORRECTION

PATENT NO. : 5,365,286
DATED : November 15, 1994
INVENTOR(S) : Takashi Masuda

It is certified that error appears in the above-indentified patent and that said Letters Patent is hereby corrected as shown below:

<u>COLUMN 6</u>

Line 51, "said" should read --wherein said--.

<u>COLUMN 7</u>

Line 4, "said" should read --wherein said--.
    Line 8, "said" should read --wherein said--.

<u>COLUMN 8</u>

Line 4, "wherein" should read --wherein said--.
    Line 26, "said" should read --wherein said--.

Signed and Sealed this

Eleventh Day of April, 1995

Attest:

BRUCE LEHMAN

*Attesting Officer*      *Commissioner of Patents and Trademarks*